United States Patent

Katayama et al.

[11] Patent Number: 5,496,794
[45] Date of Patent: Mar. 5, 1996

[54] FLUORINE-CONTAINING β-INDOLEBUTYRIC ACID COMPOUNDS, AND REGULATION OF PLANT GROWTH THEREWITH

[75] Inventors: Masato Katayama; Shozo Fujii, both of Nagoya; Hiroshi Kimoto, Kuwana; Katsuya Kato, Nagoya, all of Japan

[73] Assignees: Agency of Industrial Science & Technology; Ministry of International Trade & Industry, both of Tokyo, Japan

[21] Appl. No.: 330,792

[22] Filed: Oct. 28, 1994

[30] Foreign Application Priority Data

Nov. 9, 1993 [JP] Japan .................................. 5-304612

[51] Int. Cl.[6] .......................... C07D 209/18; A01N 43/38
[52] U.S. Cl. ............................................. 504/284; 548/494
[58] Field of Search ................................ 548/494; 504/284

[56] References Cited

FOREIGN PATENT DOCUMENTS

| | | |
|---|---|---|
| 0256128 | 2/1988 | European Pat. Off. . |
| 5-279331 | 10/1993 | Japan . |
| 1004661 | 9/1965 | United Kingdom . |

OTHER PUBLICATIONS

Michael Bottger, et al., "Growth of Avena Coleptiles and pH Drop of Protoplast Suspensions Induced by Chlorinated Indoleacetic Acids", *Planta: An International Journal of Plant Biology*, vol. 140, No. 1, 1978, pp. 89–92.

Chemical Abstracts, vol. 95, No. 7, 1981, AN 62031f, p. 704.

Chemical Abstracts, vol. 73, No. 21, 1970, AN 109613k, p. 356.

Chemical Abstracts, vol. 120, No. 13, Mar. 28, 1994, AN 163976h, p. 1162 & JP-A-05 279 331, Oct. 26, 1993.

Journal of Fermentation and Bioengineering, vol. 76, No. 3, 1993, pp. 178–183, Katsuya Kato, et al., "Enzymatic Preparation of Both Enantiomers of 4,4,4-Trifluoro-3-(Indole-3-)Butyric Acid, a Novel Plant Growth Regulator".

*Primary Examiner*—David B. Springer
*Attorney, Agent, or Firm*—Oblon, Spivak, McClelland, Maier, & Neustadt

[57] ABSTRACT

A substituted fluorine-containing β-indolebutyric acid compound represented by the formula:

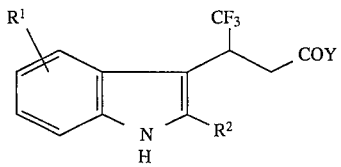

wherein Y stands for one member selected from the group consisting of hydroxyl group, alkoxy group, amino group, and alkylamino group, at least one of $R^1$ and $R^2$ stands for one member selected from the group consisting of halogen atom, alkyl group, alkoxy group, aryl group, nitro group, amino group, and alkylamino group, and the remaining one, if any, for a hydrogen atom, a plant growth regulating agent having as a substantial main component thereof the substituted fluorine-containing β-indolebutyric acid compound, and a method for regulating the length of roots sprouting from plant seeds and the length of hypocotyls by causing adhesion of the substituted fluorine-containing β-indolebutyric acid compound to the plant seeds.

10 Claims, No Drawings

FLUORINE-CONTAINING β-INDOLEBUTYRIC ACID COMPOUNDS, AND REGULATION OF PLANT GROWTH THEREWITH

BACKGROUND OF THE INVENTION

1. Field of the Invention

This invention relates to a novel substituted fluorine-containing β-indolebutyric acid compound having a physiologically active capacity for markedly elongating plant roots, a plant growth regulating agent containing the substituted fluorine-containing β-indolebutyric acid compound as an active component thereof, and a method for regulating the length of roots sprouting from plant seeds and the length of hypocotyls by the action of the compound.

2. Description of the Prior Art

It has long been known that indole-3-acetic acid (hereinafter referred to as "IAA") and derivatives thereof such as, for example, methyl indole-3-acetate and indole-3-acetamide, accelerate the growth of plants. It is also known that 4,7-dichloroindole-3-acetic acid and 5,7-dichloroindole-3-acetic acid manifest an anti-auxin action ["Planta," Vol. 140, page 89 (1978)].

It has been recently ascertained that 4,4,4-trifluoro-3-(indole-3-)butyric acid (hereinafter referred to as "TFIBA"), 4,4,4-trifluoro-2-hydroxy-3-(indole-3-)butyric acid ("TFIHBA"), and 4,4,4-trifluoro-3-(indole-3-)butyronitrile ("TFIBN"), which are fluorine-containing β-indolebutyric acid compounds, manifest a strong activity in accelerating the growth of plant roots (Collection of monographs for publication at the 1990 general meeting of Plant Chemical Regulation Society, page 31, published by Plant Chemical Regulation Society). In Japanese Patent Public Disclosure Hei 5(1993)-279331, some of the present inventors have disclosed fluorine-containing indolebutyric acid compounds which manifest a similar effect.

In the recent years, increasing the yield of plants which are useful as food has become an important task in view of the growth of the world's population. The acceleration of the elongation of plant roots is one of the factor necessary for increasing plant yield. Plant growth regulating agents containing such compounds as IAA and exhibiting anti-auxin activity and other conventional plant growth regulating agents are, however, not sufficiently active in elongating plant roots. The TFIBA, TFIHBA, and TFIBN mentioned above are fluorine-containing β-indolebutyric acid compounds that exhibit fairly strong plant root elongation activity, as compared with IAA and the derivatives thereof. Nevertheless, their activity is not fully satisfactory for practical use. A need exists for developing a substance capable of exhibiting even stronger plant root elongation activity.

SUMMARY OF THE INVENTION

This invention was accomplished in light of the foregoing circumstances. It is, therefore, an object of this invention to provide a novel compound exhibiting a physiological activity of markedly elongating plant roots, a plant growth regulating agent containing the compound as an active component thereof, and a method for accelerating the growth of plants.

The present inventors made a study in search of compounds possessing plant root elongation activity. They consequently found that substituted fluorine-containing β-indolebutyric acid compounds having specific structures provide markedly elongate plant roots as compared with the conventional fluorine-containing β-indolebutyric acid compounds. This invention has been completed on the basis of this knowledge.

Specifically, this invention is directed to a substituted fluorine-containing β-indolebutyric acid compound represented by the formula:

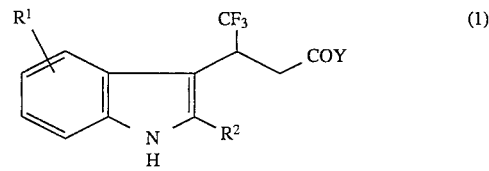

(wherein Y stands for one member selected from the group consisting of hydroxyl group, alkoxy group, amino group, and alkylamino group, at least one of $R^1$ and $R^2$ stands for one member selected from the group consisting of halogen atom, alkyl group, alkoxy group, aryl group, nitro group, amino group, and alkylamino group, and the remaining one, if any, for a hydrogen atom), a plant growth regulating agent having the substituted fluorine-containing β-indolebutyric acid compound as a substantial main component thereof, and a method for regulating the length of roots sprouting from seeds and the length of hypocotyls by causing adhesion of the substituted fluorine-containing β-indolebutyric acid compound to plant seeds.

DESCRIPTION OF THE PREFERRED EMBODIMENTS

A typical example of the method for the preparation of the substituted fluorine-containing β-indolebutyric acid compound of this invention represented by the formula (1) will now be described.

First, diethyl malonate is dissolved in toluene or benzene, for example, and to the resultant solution is added metallic sodium and desirably refluxed thermally to obtain a compound of the following formula.

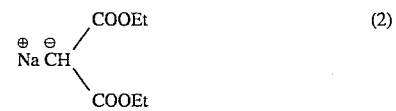

From this compound, the substituted fluorine-containing β-indolebutyric acid compound of this invention is obtained by the following reactions.

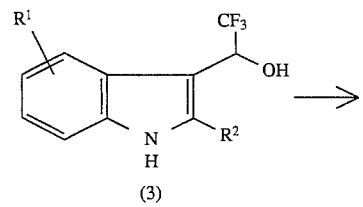

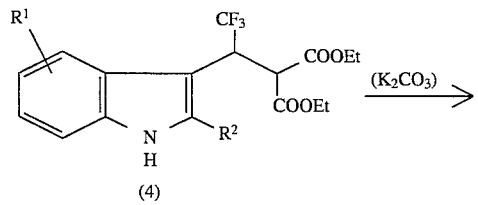

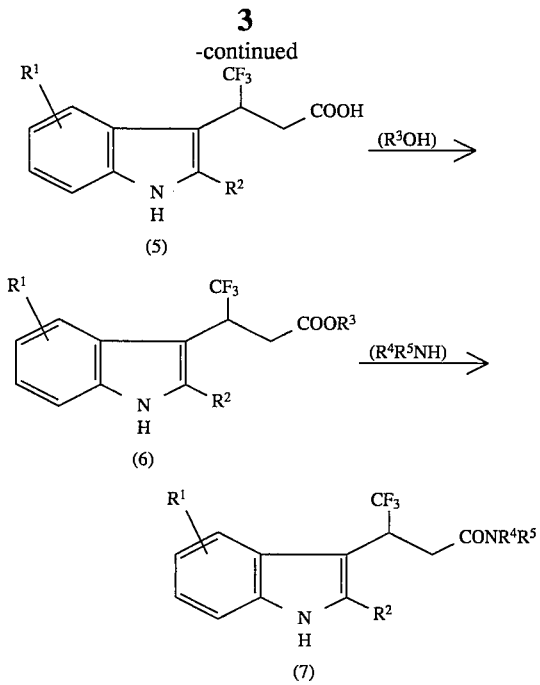

wherein $R^1$ and $R^2$ have the same meanings as defined above, $R^3$ stands for an alkyl group, $R^4$ and $R^5$ independently stand for a hydrogen atom or an alkyl group, and Et stands. for an ethyl group.

Now, the reactions mentioned above will be explained.

A compound represented by the formula (2) and 2,2,2-trifluoro-1-(substituted indole-3-)ethanol represented by the formula (3) are jointly refluxed thermally to obtain a diester represented by the formula (4). Then, this diester is dissolved in a lower alcohol (such as methanol). The resultant solution and an aqueous solution of an alkali, preferably an alkali carbonate (such as potassium carbonate), are jointly refluxed thermally to obtain a fluorine-containing β-indolebutyric acid compound of the present invention represented by the formula (5) [assuming that Y in the formula (1) is OH]. When the compound of this invention represented by the formula (5) is further heated together with an alcohol in the presence of a catalyst, preferably an acid, an ester of a fluorine-containing β-indolebutyrate of this invention represented by the formula (6) [assuming that Y in the formula (1) is $OR^3$] is obtained. When the compound represented by the formula (6) is heated together with an amine, a fluorine-containing β-indolebutyramide of this invention represented by the formula (7) [assuming that Y in the formula (1) is $NR^4R^5$] is obtained.

For the practical use of the relevant compound, the number of carbon atoms of the alkoxy group represented by Y is preferably in the range of from 1 to 5 and that of the alkylamino group similarly represented in the range of from 1 to 4, the halogen atom represented independently by $R^1$ and $R^2$ is preferably fluorine, chlorine, bromine, or iodine, the number of carbon atoms of the alkyl group similarly represented is preferably in the range of from 1 to 5, that of the alkoxy group similarly represented in the range of from 1 to 5, that of the aryl group similarly represented in the range of from 6 to 8, and that of the alkylamino group similarly represented in the range of from 1 to 4, the number of carbon atoms of the alkyl group represented by $R^3$ is preferably in the range of from 1 to 5, and the number of carbon atoms of the alkyl group represented independently by $R^4$ and $R^5$ is preferably in the range of from 0 to 4.

The 2,2,2-trifluoro-1-(substituted indole-3-)-ethanol represented by the aforementioned formula (3) can be produced by using any of the known methods, such as the methods disclosed in "Journal of Fluorine Chemistry", Vol 39, pp 47 to 59 (1988) and "Report of Nagoya Industrial Science and Technology Laboratory", Vol. 41, pp. 185 to 195 (1992).

The substituted fluorine-containing β-indolebutyric acid compounds represented by the formula (1) are novel compounds not published to date in the literature and have been identified by the procedures as shown in the working examples.

Specific examples of the main substituted fluorine-containing β-indolebutyric acid compounds mentioned above are shown in Table 1 below.

TABLE 1

| No. | $R^1$ | $R^2$ | Y | Compound |
|---|---|---|---|---|
| 1 | H | $CH_3$ | OH | 4,4,4,-trifluoro-3-(2-methylindole-3-)butyric acid |
| 2 | H | $CH_3$ | $OC_2H_5$ | ethyl 4,4,4,-trifluoro-3-(2-methylindole-3-)butyrate |
| 3 | H | $CH_3$ | $OC_3H_7$ | propyl 4,4,4,-trifluoro-3-(2-methylindole-3-)butyrate |
| 4 | H | $CH_3$ | $OC_3H_7$-iso | isopropyl 4,4,4,-trifluoro-3-(2-methylindole-3-)butyrate |
| 5 | H | $CH_3$ | $NH_2$ | 4,4,4,-trifluoro-3-(2-methylindole-3-)butyramide |
| 6 | H | $C_6H_5$ | OH | 4,4,4,-trifluoro-3-(2-phenylindole-3-)butyric acid |
| 7 | H | $C_6H_5$ | $OC_2H_5$ | ethyl 4,4,4,-trifluoro-3-(2-phenylindole-3-)butyrate |
| 8 | H | $C_6H_5$ | $OC_3H_7$ | propyl 4,4,4,-trifluoro-3-(2-phenylindole-3-)butyrate |
| 9 | H | $C_6H_5$ | $OC_3H_7$-iso | isopropyl 4,4,4,-trifluoro-3-(2-phenylindole-3-)butyrate |
| 10 | 5-Br | H | OH | 4,4,4,-trifluoro-3-(5-bromoindole-3-)butyric acid |
| 11 | 5-$CH_3O$ | H | OH | 4,4,4,-trifluoro-3-(5-methoxyindole-3-)butyric acid |
| 12 | 4-$CH_3$ | H | OH | 4,4,4,-trifluoro-3-(4-methylindole-3-)butyric acid |
| 13 | 5-$CH_3$ | H | OH | 4,4,4,-trifluoro-3-(5-methylindole-3-)butyric acid |
| 14 | 6-$CH_3$ | H | OH | 4,4,4,-trifluoro-3-(6-methylindole-3-)butyric acid |
| 15 | 7-$CH_3$ | H | OH | 4,4,4,-trifluoro-3-(7-methylindole-3-)butyric acid |
| 16 | 5-$CH_3O$-2-$CH_3$ | H | OH | 4,4,4,-trifluoro-3-(5-methoxy-2-methylindole-3-)butyric acid |

The substituted fluorine-containing β-indolebutyric acid compounds of this invention represented by the aforementioned formula (1) are superior to the conventional fluorine-containing β-indolebutyric acid compounds TFIBA, TFI-HBA, and TFIBN in activity of accelerating the elongation of plant roots.

The plant growth regulating agent of this invention has a substituted fluorine-containing β-indolebutyric acid compound of this invention as the substantial main component thereof. It may be used in its unmodified form. Otherwise, it may be mixed with auxiliaries generally used in agricultural pesticides for promoting or stabilizing the effect thereof and put to use in various forms such as solution, dust, granules, wettable agent, flowable agent, or emulsion.

These preparations are put to actual use in their unmodified form or as diluted with water to a prescribed concentration.

When the substituted fluorine-containing β-indolebutyric acid compound of this invention is used in a plant growth regulating agent, it is generally used at a concentration in the range of from $1\times10^{-6}$M to $1\times10^{-2}$M. However, the concentration does not have to be confined within this range.

The roots of a plant form one of its alimentary organs for absorbing water and nutrients under ground and also serve to support the aerial part of the plant. The substituted fluorine-containing β-indolebutyric acid compound of this invention is a novel compound which exhibits a physiological activity of markedly elongating the plant roots. It can be used as a plant growth regulating agent capable of manifesting its effect at a lower concentration than the known compounds. This plant growth regulating agent manifests the activity of producing marked elongation of roots during the initial stage of germination and, owing to this activity, enhances the ability of plants to resist external forces tending to flatten them on the grounds and provides excellent effects (increased crop yield, accelerated maturity, and enlarged fruit)by promoting the growth of the entire plant including the aerial parts thereof.

This invention will now be described more specifically below with reference to working examples.

EXAMPLE 1

Preparation of 4,4,4-trifluoro-3-(2-methylindole-3-)butyric acid [Compound of formula (1) with OH for Y, H for $R^1$, and $CH^3$ for $R^2$]

A solution of 88.5 g (555 mmol) of diethyl malonate in 300 ml of toluene and 12.7 g of metallic sodium were jointly refluxed thermally for two hours. The reflux product and 42.3 g (185 mmol) of 2,2,2-trifluoro-1-(2-methylindole-3-)ethanol [compound of formula (3) with H for $R^1$ and $CH_3$ for $R^2$] were jointly refluxed thermally for 20 hours. The reflux product was treated with methanol to decompose the unreacted sodium. The reaction mixture consequently obtained was neutralized with 4N-hydrochloric acid. The aqueous solution which was obtained by concentrating the neutralized solution was acidified with 4N-hydrochloric acid and extracted four times with ethyl acetate. Then, the ethyl acetate layer was washed with water and saturated saline solution, dried with anhydrous sodium sulfate, and then concentrated under reduced pressure to obtain oily crude diester of dicarboxylic acid [compound of formula (4) with H for $R^1$ and $CH_3$ for $R^2$]. This crude diester was dissolved in 200 ml of methanol. This methanol solution and a solution of 127.6 g (925 mmol) of potassium carbonate in 100 ml of water were jointly refluxed thermally for 48 hours. The resultant solution was cooled to room temperature, then neutralized with 4N-hydrochloric acid, and concentrated under vacuum to obtain an aqueous solution. This aqueous solution was alkalinized with 4N-sodium hydroxide solution and treated three times with ethyl acetate. The aqueous solution consequently obtained was acidified with 4N-hydrochloric acid and extracted with ethyl acetate. Then, the ethyl acetate layer was washed with water, dried with anhydrous sodium sulfate, and concentrated under vacuum. The crude indolebutyric acid compound thus obtained was refined by the treatment of silica gel column chromatography and recrystallized with ethyl acetate/n-hexane. Consequently, 38.8 g of 4,4,4-trifluoro-3-(2-methylindole-3-)butyric acid of this invention was obtained (yield 77.4%).

The melting point of this compound was 148° to 149° C. The infrared absorption spectrum, mass spectrum, and the result of $^1$H-NMR measurement of this compound were as follows.

$IRv_{max}^{KBr}$ (cm$^{-1}$): 3475, 3420, 3060, 2930, 1713, 1460, 1430, 1310, 1260, 1150, 1110, 1020, 750, 630 465 MS (70 ev): 271 (M$^+$, 85%) 251 (6) 226 (5) 212 (100), 202 (39), 160 (10), 156 (12), 130 (12) $^1$H-NMR (200 MHz), TMS, aceton-d$_6$): 2.95~3.25 (3H, m), 4.35 (1H, m), 7.00~7.25 (2H, m), 7.40~7.55 (2H, m), 7.69 (1H, d, J=7.0 Hz)

EXAMPLE 2

Preparation of ethyl 4,4,4-trifluoro-3-(2-methylindole-3-)butyrate [Compound of formula (1) with OC$_2$H$_5$ for Y, H for $R^1$, and CH$_3$ for $R^2$]

2.21 g (8.18 mmol) of the 4,4,4-trifluoro-3-(2-methylindole-3-)butyric acid obtained in Example 1 was dissolved in 50 ml of ethanol. The resultant solution, with 0.05 ml of concentrated sulfuric acid added, was refluxed thermally for 11 hours, then thrown into the water, and extracted three times with ether. Subsequently, the ether layer was washed with water and saturated saline solution, dried with anhydrous sodium sulfate, and then concentrated under a reduced pressure. The oily crude ethyl ester consequently obtained was refined by the treatment of silica gel column chromatography and recrystallized with carbon tetrachloride/hexane. Consequently, 2.40 g of ethyl 4,4,4-trifluoro-3-(2-methylindole-3-)butyrate of this invention was obtained (yield 98.0%).

The melting point of this compound was 71° to 71.5° C. The infrared absorption spectrum, mass spectrum, and the result of $^1$H-NMR measurement of this compound were as follows.

$IRv_{max}^{KBr}$ (cm$^{-1}$): 3360, 1710, 1460, 1420, 1315, 1295, 1265, 1230, 885, 718, 650 MS (70 ev): 299 (M$^+$, 100%) 254 (10) 230 (25), 212 (92), 157 (14) $^1$H-NMR (90 MHz), TMS, acetone-d$_6$): 1.03 (3H, t, J=7.0 Hz), 2.46 (3H, s), 3.16 (2H, d, J=7.2 Hz), 4.01 (2H, q, J=7.0 Hz), 4.27 (1H, t-d, J=10.5 and 7.2 Hz), 6.9~7.6 (4H, m), 10.05 (1H, brs)

EXAMPLE 3

Preparation of 4,4,4-trifluoro-3-(2-methylindole-3-)butyramide [Compound of formula (1) with NH$_2$ for Y, H for $R^1$, and CH$_3$ for $R^2$]

0.60 g (2.0 mmol) of the ethyl 4,4,4-trifluoro-3-(2-methylindole-3-)butyrate obtained in Example 2 was dissolved in 5 ml of methanol. The resultant solution and 20 ml of an aqueous 28 wt % ammonia solution added thereto were stirred and heated at 35° C. for six hours to induce a reaction. The resultant reaction mixture was cooled with ice, combined with saturated saline solution, and extracted four times with ethyl acetate. Then, the ethyl acetate layer was washed with saturated saline solution, dried with anhydrous sodium sulfate, and concentrated under a reduced pressure to obtain a substantially pure amide compound. This amide compound was recrystallized with ethyl acetate/hexane. Consequently, 0.39 g (yield 71.9%) of 4,4,4-trifluoro-3-(2-methylindole-3-)butyramide of this invention was obtained.

The melting point of this compound was 177° to 177.5° C. The infrared absorption spectrum, mass spectrum, and result of $^1$H-NMR measurement of this compound were as follows.

$IRv_{max}^{KBr}$ (cm$^{-1}$): 3500, 3380, 3250, 1685, 1675, 1465, 1340, 1260, 1155, 1105, 1025, 755, 445 MS (70 ev): 271 (M$^+$, 14%) 270 (M$^+$, 93%) 250 (34), 226 (17), 213 (14), 212 (100), 211 (21), 201 (9), 158 (25), 157 (14) $^1$H-NMR (90 MHZ), TMS, acetone-d$_6$): 2.40 (3H, s), 3.18 (2H, s), 4.38

(1H, m), 6.29 (1H, brs), 6.9~7.1 (3H, m), 7.2~7.6 (2H, m), 10.08 (1H, brs)

The yield and the melting points of the typical fluorine-containing β-indolebutyric acids of this invention represented by the formula (1) are shown in Table 2.

| No. | Yield (%) | Melting point (°C.) |
|---|---|---|
| 1 | 77.4 | 148–149 |
| 2 | 98.1 | 71–71.5 |
| 3 | 94.8 | 82–83 |
| 4 | 92.3 | 61–62 |
| 5 | 71.9 | 177–177.5 |
| 6 | 56.6 | 165–167 |
| 7 | 88.5 | 114–115 |
| 8 | 90.6 | 97–98 |
| 9 | 91.7 | 138–139 |
| 10 | 82.4 | 171–173 |
| 11 | 81.7 | 169–171 |
| 12 | 75.8 | 146–148 |
| 13 | 82.0 | 143–145 |
| 14 | 87.3 | 137–139 |
| 15 | 80.5 | 95–97 |
| 16 | 70.5 | 133–134 |

Test Example

Biological test using Chinese cabbage

The samples used in this test were 2-Me-TFIBA [compound of formula (1) with OH for Y, H for $R^1$, and $CH_3$ for $R^2$], 5-Me-TFIBA [compound of formula (1) with OH for Y, 5-$CH_3$ for $R^1$, and H for $R^2$], 5-MeO-2-Me-TFIBA [compound of formula (1) with OH for Y, 5-$OCH_3$ for $R^1$ and $CH_3$ for $R^2$], 5-MeO-TFIBA [compound of formula (1) with OH for Y, 5-$OCH_3$ for $R^1$ and H for $R^2$], and 5-Br-TFIBA [compound of formula (1) with OH for Y, 5-Br for $R^1$ and H for $R^2$], and TFIBA was used as the compared compound.

Seeds of Chinese cabbage (species: Kinshu) were rinsed with distilled water, sown on absorbent cotton thoroughly wetted with distilled water in a petri dish, and left standing at 25° C. for about 24 hours. In petri dishes 6 cm in diameter, solutions (4 ml) containing the samples and TFIBA as the control severally at concentrations of $10^{-6}$, $10^{-5}$, $10^{-4}$, and $10^{-3}$ (M) were placed one each, filter papers (5.5 cm in diameter) were laid in the solutions, and the seeds (germinated) which had sprouted roots to a slight extent in consequence of the treatment described above were set in place at the rate of 10 pieces per solution on the wetted filter papers and incubated for three days under the conditions of 25° C., 6,000 lux, and 16-hour days. The roots and the hypocotyls growing from the seeds were examined to determine their lengths. The results are shown in Table 3.

TABLE 3

| Compound [Formula (1) Y = OH] | Concentration (M) | Root length (cm) | (%) | Hypocotyl length (cm) | (%) |
|---|---|---|---|---|---|
| TFIBA (compared compound) | $10^{-6}$ | 25.6 | 143.3 | 6.7 | 124.4 |
| | $10^{-5}$ | 29.0 | 162.0 | 6.9 | 127.8 |
| | $10^{-4}$ | 53.1 | 296.6 | 6.4 | 118.5 |
| | $10^{-3}$ | 5.0 | 27.9 | 7.6 | 140.7 |
| 2-Me-TFIBA ($R^1$ = H, $R^2$ = $CH_3$) | $10^{-6}$ | 25.1 | 140.2 | 5.4 | 100.0 |
| | $10^{-5}$ | 46.2 | 258.1 | 6.2 | 114.8 |
| | $10^{-4}$ | 65.0 | 363.1 | 7.9 | 146.3 |
| | $10^{-3}$ | 2.0 | 11.2 | 4.4 | 81.5 |
| 5-Me-TFIBA ($R^1$ = 5-$CH_3$, $R^2$ = H) | $10^{-6}$ | 21.9 | 122.8 | 5.4 | 100.0 |
| | $10^{-5}$ | 41.4 | 231.3 | 6.4 | 118.5 |
| | $10^{-4}$ | 65.7 | 367.0 | 6.7 | 124.1 |
| | $10^{-3}$ | 1.0 | 5.6 | 5.8 | 107.4 |
| 5-MeO-2-Me-TFIBA ($R^1$ = 5-$OCH_3$, $R^2$ = $CH_3$) | $10^{-6}$ | 20.6 | 115.1 | 5.4 | 100.0 |
| | $10^{-5}$ | 32.3 | 180.4 | 5.7 | 105.6 |
| | $10^{-4}$ | 75.9 | 424.0 | 7.7 | 142.6 |
| | $10^{-3}$ | 3.3 | 18.4 | 6.4 | 118.5 |
| 5-MeO-TFIBA ($R^1$ = 5-$OCH_3$, $R^2$ = H) | $10^{-6}$ | 19.6 | 109.5 | 5.7 | 105.6 |
| | $10^{-5}$ | 19.7 | 110.1 | 5.7 | 105.6 |
| | $10^{-4}$ | 54.4 | 303.9 | 5.4 | 100.0 |
| | $10^{-3}$ | 1.7 | 9.5 | 7.0 | 129.6 |
| 5-Br-TFIBA ($R^1$ = 5-Br, $R^2$ = H) | $10^{-6}$ | 20.0 | 111.7 | 5.7 | 105.6 |
| | $10^{-5}$ | 41.6 | 323.4 | 5.6 | 103.7 |
| | $10^{-4}$ | 51.3 | 286.6 | 5.6 | 103.7 |
| | $10^{-3}$ | 0.0 | 0.0 | 4.5 | 83.3 |
| None (control) | | 17.9 | 100.0 | 5.4 | 100.0 |

It can be seen from Table 3 that the substituted fluorine-containing β-indolebutyric acid compounds of this invention manifest a strong activity of accelerating elongation of plant roots. From a comparison of the results obtained of the samples with those of the compared compound, i.e. TFIBA, which is a fluorine-containing β-indolebutyric acid having no substituting group in the indole ring, it is noted that the introduction of a substituting group into the indole ring enhances the activity of accelerating the elongation, specifically that the introduction of an electron-donating substituting group and the introduction of a substituting group at the 2 position are particularly effective for enhancing the activity of accelerating the elongation of plant roots, and that the substituted fluorine-containing β-indolebutyric acid compounds manifest the enhanced activity of accelerating the elongation of plant roots even at a low application rate.

What is claimed is:

1. A substituted fluorine-containing β-indolebutyric acid compound represented by the formula:

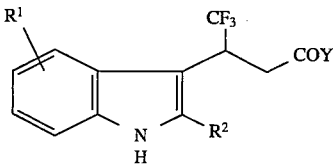

wherein Y stands for one member selected from the group consisting of hydroxyl group, $C_1$–$C_5$-alkoxy group, amino group, and $C_1$–$C_4$-alkylamino group, $R^1$ and $R^2$ stand for one member selected from the group consisting of hydrogen atom, halogen atom, $C_1$–$C_5$-alkyl group, $C_1$–$C_5$-alkoxy group, $C_6$–$C_8$-aryl group, nitro group, amino group, and $C_1$–$C_4$-alkylamino group, provided $R_1$ and $R_2$ are not both a hydrogen atom.

2. A substituted fluorine-containing β-indolebutyric acid compound according to claim 1, wherein the number of carbon atoms of the alkoxy group represented by Y is in the range of from 1 to 5 and that of the alkylamino group similarly represented in the range of from 1 to 4, the halogen atom represented independently by $R^1$ and $R^2$ is fluorine, chlorine, bromine, or iodine, the number of carbon atoms of the alkyl group similarly represented is in the range of from 1 to 5, that of the alkoxy group similarly represented in the range of from 1 to 5, that of the aryl group similarly represented in the range of from 6 to 8, and that of the alkylamino group similarly represented in the range of from 1 to 4.

3. A substituted fluorine-containing β-indolebutyric acid compound according to claim 1, which is selected from the group consisting of 4,4,4-trifluoro-3-(2-methylindole-3-)butyric acid, ethyl 4,4,4-trifluoro-3-(2-methylindole-3-)butyrate, propyl 4,4,4-trifluoro-3-(2-methylindole-3-)butyrate, isopropyl 4,4,4-trifluoro-3-(2-methylindole-3-)butyrate, 4,4,4-trifluoro-3-(2-methylindole-3-)butyramide, 4,4,4-trifluoro-3-(2-phenylindole-3-)butyric acid, ethyl 4,4,4-trifluoro-3-(2-phenylindole-3-)butyrate, propyl 4,4,4-trifluoro-3-(2-phenylindole-3-)butyrate, isopropyl 4,4,4-trifluoro-3-(2-phenylindole-3-)butyrate, 4,4,4-trifluoro-3-(5-bromoindole-3-)butyric acid, 4,4,4-trifluoro-3-(5-methoxyindole-3-)butyric acid, 4,4,4-trifluoro-3-(4-methylindole-3-)butyric acid, 4,4,4-trifluoro-3-(5-methylindole-3-)butyric acid, 4,4,4-trifluoro-3-(6-methylindole-3-)butyric acid, 4,4,4-trifluoro-3-(7-methylindole-3-)butyric acid, and 4,4,4-trifluoro-3-(5-methoxy-2-methylindole-3-)butyric acid.

4. A plant growth regulating agent comprising a substituted fluorine-containing β-indolebutyric acid compound represented by the formula:

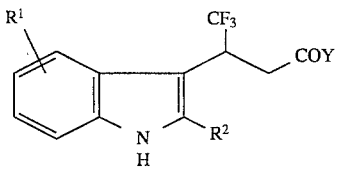

wherein Y stands for one member selected from the group consisting of hydroxyl group, $C_1$–$C_5$-alkoxy group, amino group, and $C_1$–$C_4$-alkylamino group, $R^1$ and $R^2$ stand for one member selected from the group consisting of hydrogen atom, halogen atom, $C_1$–$C_5$-alkyl group, $C_1$–$C_5$-alkoxy group, $C_6$–$C_8$-aryl group, nitro group, amino group, and $C_1$–$C_4$-alkylamino group, provided $R^1$ and $R^2$ are not both a hydrogen atom.

5. A plant growth regulating agent according to claim 4, wherein the number of carbon atoms of the alkoxy group represented by Y is in the range of from 1 to 5 and that of the alkylamino group similarly represented in the range of from 1 to 4, the halogen atom represented independently by $R^1$ and $R^2$ is fluorine, chlorine, bromine, or iodine, the number of carbon atoms of the alkyl group similarly represented is in the range of from 1 to 5, that of the alkoxy group similarly represented in the range of from 1 to 5, that of the aryl group similarly represented in the range of from 6 to 8, and that of the alkylamino group similarly represented in the range of from 1 to 4.

6. A plant growth regulating agent according to claim 4 having as a substantial main component thereof a substituted fluorine-containing β-indolebutyric acid compound selected from the group consisting of 4,4,4-trifluoro-3-(2-methylindole-3-)butyric acid, ethyl 4,4,4-trifluoro-3-(2-methylindole-3-)butyrate, propyl 4,4,4-trifluoro-3-(2-methylindole-3-)butyrate, isopropyl 4,4,4-trifluoro-3-(2-methylindole-3-)butyrate, 4,4,4-trifluoro-3-(2-methylindole-3-)butyramide, 4,4,4-trifluoro-3-(2-phenylindole-3-)butyric acid, ethyl 4,4,4-trifluoro-3-(2-phenylindole-3-)butyrate, propyl 4,4,4-trifluoro-3-(2-phenylindole-3-)butyrate, isopropyl 4,4,4-trifluoro-3-(2-phenylindole-3-)butyrate, 4,4,4-trifluoro-3-(5-bromoindole-3-)butyric acid, 4,4,4-trifluoro-3-(5-methoxyindole-3-)butyric acid, 4,4,4-trifluoro-3-(4-methylindole-3-)butyric acid, 4,4,4-trifluoro-3-(5-methylindole-3-)butyric acid, 4,4,4-trifluoro-3-(6-methylindole-3-)butyric acid, 4,4,4-trifluoro-3-(7-methylindole-3-)butyric acid, and 4,4,4-trifluoro-3-(5-methoxy-2-methylindole-3-)butyric acid.

7. A method for regulating the length of roots sprouting from plant seeds and the length of hypocotyls, which comprises causing adhesion to said plant seeds of a substituted fluorine-containing β-indolebutyric acid compound represented by the formula:

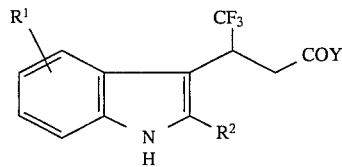

wherein Y stands for one member selected from the class consisting of hydroxyl group, $C_1$–$C_5$-alkoxy group, amino group, and $C_1$–$C_4$-alkylamino group, $R^1$ and $R^2$ stand for one member selected from the class consisting of hydrogen atom, halogen atom, $C_1$–$C_5$-alkyl group, $C_1$–$C_5$-alkoxy group, $C_6$–$C_8$-aryl group, nitro group, amino group, and $C_1$–$C_4$-alkylamino group, provided $R^1$ and $R^2$ are not both a hydrogen atom.

8. A method according to claim 7, wherein the number of carbon atoms of the alkoxy group represented by Y is in the range of from 1 to 5 and that of the alkylamino group similarly represented in the range of from 1 to 4, the halogen atom represented independently by $R^1$ and $R^2$ is fluorine, chlorine, bromine, or iodine, the number of carbon atoms of the alkyl group similarly represented is in the range of from 1 to 5, that of the alkoxy group similarly represented in the range of from 1 to 5, that of the aryl group similarly represented in the range of from 6 to 8, and that of the alkylamino group similarly represented in the range of from 1 to 4.

9. A method according to claim 7, wherein said substituted fluorine-containing β-indolebutyric acid compound is selected from the group consisting of 4,4,4-trifluoro-3-(2-methylindole-3-)butyric acid, ethyl 4,4,4-trifluoro-3-(2-methylindole-3-)butyrate, propyl 4,4,4-trifluoro-3-(2-methylindole-3-)butyrate, isopropyl 4,4,4-trifluoro-3-(2-methylindole-3-)butyrate, 4,4,4-trifluoro-3-(2-methylindole-3-)butyramide, 4,4,4-trifluoro-3-(2-phenylindole-3-)butyric acid, ethyl 4,4,4-trifluoro-3-(2-phenylindole-3-)butyrate, propyl 4,4,4-trifluoro-3-(2-phenylindole-3-)butyrate, isopropyl 4,4,4-trifluoro-3-(2-phenylindole-3-)butyrate, 4,4,4-trifluoro-3-(5-bromoindole-3-)butyric acid, 4,4,4-trifluoro-3-(5-methoxyindole-3-)butyric acid, 4,4,4-trifluoro-3-(4-methylindole-3-)butyric acid, 4,4,4-trifluoro-3-(5-methylindole-3-)butyric acid, 4,4,4-trifluoro-3-(6-methylindole-3-)butyric acid, 4,4,4-trifluoro-3-(7-methylindole-3-)butyric acid, and 4,4,4-trifluoro-3-(5-methoxy-2-methylindole-3-)butyric acid.

10. A method according to claim 7, wherein said substituted fluorine-containing β-indolebutyric acid compound is caused to contact the plant seeds at a concentration in the range of from $1 \times 10^{-6}$M to $1 \times 10^{-2}$M.

* * * * *

UNITED STATES PATENT AND TRADEMARK OFFICE
CERTIFICATE OF CORRECTION

PATENT NO. : 5,496,794
DATED : March 5, 1996
INVENTOR(S) : Masato KATAYAMA et al.

It is certified that error appears in the above-indentified patent and that said Letters Patent is hereby corrected as shown below:

On the title page, Item [73], the Assignee is written incorrectly. It should read:

--[73] Assignee: Agency of Industrial Science & Technology, Ministry of International Trade & Industry, Tokyo, Japan--

Signed and Sealed this

Eleventh Day of June, 1996

Attest:

BRUCE LEHMAN

Attesting Officer

Commissioner of Patents and Trademarks